United States Patent
Wolfgramm et al.

(10) Patent No.: US 12,036,349 B2
(45) Date of Patent: Jul. 16, 2024

(54) OPTICAL LEVEL CONTROL SYSTEM

(71) Applicant: LivaNova Deutschland GmbH, Munich (DE)

(72) Inventors: Olivier Wolfgramm, Munich (DE); Michael Bonczar, Ampfing (DE); Marco Zanasi, Bologna (IT)

(73) Assignee: LivaNova Deutschland GmbH, Munich (DE)

( * ) Notice: Subject to any disclaimer, the term of this patent is extended or adjusted under 35 U.S.C. 154(b) by 0 days.

(21) Appl. No.: 18/070,722

(22) Filed: Nov. 29, 2022

(65) Prior Publication Data

US 2023/0090797 A1    Mar. 23, 2023

Related U.S. Application Data

(63) Continuation of application No. 16/959,109, filed as application No. PCT/EP2018/082237 on Nov. 22, 2018, now Pat. No. 11,541,160.

(30) Foreign Application Priority Data

Jan. 15, 2018 (EP) .................................... 18151587

(51) Int. Cl.
*A61M 1/36* (2006.01)
*G01F 23/00* (2022.01)
(Continued)

(52) U.S. Cl.
CPC ........ *A61M 1/3666* (2013.01); *A61M 1/3607* (2014.02); *A61M 1/3624* (2013.01);
(Continued)

(58) Field of Classification Search
CPC ........ G01F 23/00; G01F 23/02; G01F 23/263; G01F 25/00; G01F 25/20; G01F 25/24;
(Continued)

(56) References Cited

U.S. PATENT DOCUMENTS

| | | | |
|---|---|---|---|
| 8,500,673 | B2 | 8/2013 | Zanotti et al. |
| 2006/0178578 | A1 | 8/2006 | Tribble et al. |

(Continued)

FOREIGN PATENT DOCUMENTS

| | | |
|---|---|---|
| DE | 19817995 C1 | 9/1999 |
| EP | 3266481 A1 | 1/2018 |
| WO | 0170304 A1 | 9/2001 |

OTHER PUBLICATIONS

International Search Report and Written Opinion received for PCT Patent Application No. PCT/EP2018/082337, dated Feb. 21, 2019, 10 pages.

*Primary Examiner* — Andre J Allen
(74) *Attorney, Agent, or Firm* — Seager, Tufte & Wickhem LLP

(57) ABSTRACT

A perfusion system includes a fluid reservoir configured to hold a portion of fluid, the portion of fluid having a volume, the fluid reservoir having a total capacity that is greater than the volume; an imaging device, the imaging device configured to obtain image data corresponding to the fluid reservoir; and a controller. The controller is configured to receive the image data from the imaging device; determine the volume based on the image data; and facilitate control, in response to at least one of a user input and the determined volume of the portion of fluid, of an operating parameter corresponding to the fluid reservoir to facilitate changing or maintaining the volume of the portion of the fluid.

20 Claims, 3 Drawing Sheets

(51) Int. Cl.
  *G01F 23/02*    (2006.01)
  *G01F 25/00*    (2022.01)
  *G01F 25/20*    (2022.01)
  *G05B 23/02*    (2006.01)
  *G06F 11/32*    (2006.01)

(52) U.S. Cl.
  CPC .............. *G01F 23/00* (2013.01); *G01F 23/02* (2013.01); *G01F 25/00* (2013.01); *G01F 25/20* (2022.01); *G01F 25/24* (2022.01); *G05B 23/02* (2013.01); *G05B 23/0216* (2013.01); *G06F 11/32* (2013.01); *G06F 11/321* (2013.01); *A61M 2205/3306* (2013.01); *A61M 2205/3379* (2013.01); *G08C 2201/30* (2013.01)

(58) Field of Classification Search
  CPC ..... G06F 11/32; G06F 11/321; A61M 1/3607; A61M 1/3624; A61M 1/3666; A61M 2205/3306; A61M 2205/3379; A61M 2205/3389; G05B 23/02; G05B 23/0216
  See application file for complete search history.

(56) References Cited

U.S. PATENT DOCUMENTS

| | | |
|---|---|---|
| 2011/0257576 A1 | 10/2011 | Simpson et al. |
| 2014/0079590 A1 | 3/2014 | Rossi et al. |
| 2015/0002667 A1 | 1/2015 | Peret et al. |
| 2015/0105642 A1 | 4/2015 | Rossi et al. |

OPTICAL LEVEL CONTROL SYSTEM

CROSS REFERENCE TO RELATED APPLICATIONS

This application is a continuation of U.S. patent application Ser. No. 16/959,109, filed Jun. 29, 2020, which is a 371 of International Application No. PCT/EP2018/082237, filed Nov. 22, 2018, which claims priority to European App. No. 18151587.5, filed Jan. 15, 2018, the disclosures of which are incorporated herein by reference.

TECHNICAL FIELD

The disclosure relates generally to perfusion and autotransfusion systems and more particularly to a blood reservoir monitored using an imaging device.

BACKGROUND

Perfusion entails encouraging physiological solutions, such as blood, through vessels in the body or some portion of the body of a human or other animal. Perfusion can be employed in intracorporeal and extracorporeal circulation, such as during cardiopulmonary bypass surgery and other surgeries and during various therapeutic treatments. Perfusion is useful in maintaining the viability of body parts, such as specific organs or limbs, while the body part remains within the body or while the body part is exterior to the body, such as for transplantation or temporarily removal of a body part to provide access to other body structures. Perfusion can be used for a short period of time, such as less than about six hours, or for extended periods of time, such as greater than about six hours.

Sometimes, blood perfusion systems include one or more pumps in an extracorporeal circuit that is interconnected with the vascular system of a patient. Typically, cardiopulmonary bypass (CPB) surgery utilizes a perfusion system that allows for the temporary cessation of the heart by replacing the functions of the heart and lungs, which creates a still operating field and allows for the surgical correction of problems, such as vascular stenosis, valvular disorders, and congenital heart and great vessel defects. Perfusion systems for cardiopulmonary bypass surgery include an extracorporeal blood circuit that includes at least one pump and an oxygenation device to replace the functions of the heart and lungs.

In cardiopulmonary bypass procedures, oxygen-poor blood is removed from a large vein entering the heart or from other veins (e.g., a femoral vein) in the body and transferred through a venous line in the extracorporeal circuit. In embodiments, the blood may be removed via drainage (e.g., by gravity-draining the blood, kinetic drainage via a pump, etc.), vacuum suctioning, and/or the like. The venous blood is pumped to an oxygenator that provides for oxygen transfer to the blood. Oxygen may be introduced into the blood by transfer across a membrane or, less frequently, by bubbling oxygen through the blood. Concurrently, carbon dioxide is removed across the membrane. The oxygenated blood is then returned through an arterial line to the aorta, femoral, or other main artery.

The perfusionist often uses level sensors only for pump emergency shut off, when the blood level in the reservoir goes below a safe minimum value. One of the perfusionist's most important tasks is to continuously keep the reservoir blood level/volume under visual control, by manually regulating the venous blood flow entering the reservoir, by acting on the venous clamp, or, if present, by alternatively acting on the vacuum applied to the reservoir. Additionally, the arterial pump may also be manually adjusted, if necessary, in order to regulate the arterial blood flow exiting the reservoir. This task requires constant attention by the perfusionist who has to keep the reservoir under strict visual control, throughout the case.

The reservoir blood level control is important in cardiac surgery. In fact, a certain amount (variable during the case, according to changing needs) of venous blood typically has to be kept in the reservoir at all time. The reservoir may have multiple shapes and sizes and may be rigid (hardshell) or flexible (soft bags). The conventional level sensors based on ultrasonic, capacitive or pressure measurements are often too large when used with very small reservoirs for neonatal cases. Additionally, they rarely have the capability to provide a continuous monitoring over the whole reservoir volume or height, but rather monitor only one level or range of levels. Furthermore conventional level sensors are not configured to translate the measured level into a volume.

SUMMARY

Embodiments of perfusion systems described herein are able to measure and control the fluid level in a fluid reservoir by providing an image of the reservoir and of the fluid contained therein on a screen (and/or an abstracted representation thereof), and by enabling user interaction with the screen image so as to provide a heart lung machine (HLM) with inputs to facilitate automatically maintaining the amount of fluid in the reservoir at a desired value. Embodiments of the system include an imaging device (e.g., optical sensor, camera, etc.) configured to reproduce an image and/or shape of the reservoir. The system may include a control panel having a display device on which the reservoir image (or reservoir representation) is shown and with which the perfusionist sets the desired working value for the fluid in the reservoir. Embodiments of the system further include an HLM control unit that, by means of a dedicated fail safe operative mode, is able to automatically maintain the fluid in the reservoir at the desired value by, for example, acting on a venous clamp, a vacuum regulator, an arterial pump, and/or the like.

In an Example 1, a perfusion system comprises: a fluid reservoir configured to hold a portion of fluid, the portion of fluid having a volume, the fluid reservoir having a total capacity that is greater than the volume; an imaging device, the imaging device configured to obtain image data corresponding to the fluid reservoir; and a controller configured to: receive the image data from the imaging device; determine the volume based on the image data; and facilitate control, in response to at least one of a user input and the determined volume of the portion of fluid, of an operating parameter corresponding to the fluid reservoir to facilitate changing or maintaining the volume of the portion of the fluid.

In an Example 2, the system of Example 1, wherein the imaging device comprises at least one of a camera, a photoconductive sensor, a photodiode, a phototransistor, a photovoltaic sensor, and a charge coupled device (CCD) sensor.

In an Example 3, the system of either of Examples 1 or 2, wherein the controller is further configured to provide, via a control panel having a display device and based on the image data, a graphical user interface (GUI), the GUI comprising a representation of the fluid reservoir, the representation of the fluid reservoir comprising a representation of the portion of fluid, the representation including a representation of the volume.

In an Example 4, the system of any of Examples 1-3, the imaging device further comprising a virtual curtain having an opening disposed therethrough, the opening having a shape that corresponds to a shape of the fluid reservoir, wherein the curtain is configured to facilitate positioning, maintaining positioning, and/or monitoring positioning of the imaging device in relation to the fluid reservoir, and/or, after setup, upon detecting dislocation of the reservoir.

In an Example 5, the system of either of Examples 3 or 4, wherein the representation of the fluid reservoir is configured to resemble a fluid reservoir, and wherein the representation of the volume is configured to resemble liquid within the fluid reservoir.

In an Example 6, the system of any of Examples 3-5, wherein the representation of the fluid reservoir is an interactive representation, and wherein the controller is configured to receive a user input associated with the interactive representation of the portion of fluid and, in response to receiving the user input, facilitate adjusting an operating parameter corresponding to the fluid reservoir to facilitate changing or maintaining the volume of the portion of fluid.

In an Example 7, the system of Example 6, wherein the user input comprises manipulation, by a user of a feature of the interactive representation of the fluid reservoir.

In an Example 8, the system of any of Examples 1-7, wherein the controller is configured to facilitate control of the operating parameter corresponding to the fluid reservoir by causing a heart lung machine (HLM) control unit to adjust an operating parameter corresponding to the fluid reservoir.

In an Example 9, the system of any of Examples 1-7, wherein the controller includes a heart lung machine (HLM) control unit, and wherein the HLM control unit is configured to adjust an operating parameter corresponding to the fluid reservoir.

In an Example 10, the system of either of Examples 8 or 9, wherein the HLM control unit is configured to control at least one of a venous clamp, a vacuum regulator, and an arterial pump.

In an Example 11, the system of any of Examples 3-10, the GUI further comprising interactive representations configured to facilitate user selection of at least one of an alarm level, an alarm volume, and a fluid volume set point.

In an Example 12, the system of any of Examples 1-11, wherein the controller is configured to facilitate control of an operating parameter corresponding to the fluid reservoir to facilitate continually changing the volume of the portion of fluid about a fluid volume set point.

In an Example 13, the system of any of Examples 1-12, wherein the controller is configured to: write a pixel test pattern to an imaging device memory, the pixel test pattern comprising a pattern of pixels having one or more pixel groups having values of at least one of color and intensity that are not expected to occur naturally in the imaging environment; and determine whether, during a next data acquisition cycle, the pixel test pattern is replaced with an acquired image.

In an Example 14, the system of any of Examples 1-13, wherein the controller is configured to detect frozen images by: generating an image test pattern; causing, using an optical mixer, the image test pattern to be projected on an image sensor of the imaging device together with the image data, the image data comprising a pattern associated with the fluid reservoir; and comparing the image test pattern to the pattern associated with the fluid reservoir, wherein, if the image test pattern is at least approximately identical to the pattern associated with the fluid reservoir, the controller is configured to accept the image data.

In an Example 15, a method of performing perfusion, using a perfusion system having a fluid reservoir configured to hold a portion of fluid, the portion of fluid having a volume, the method comprising: receiving, by a controller and from an imaging device, image data corresponding to the fluid reservoir; determining the volume based on the image data; providing, via a control panel having a display device and based on the image data, a graphical user interface (GUI), the GUI comprising a representation of the fluid reservoir, the representation of the fluid reservoir comprising a representation of the portion of fluid, the representation including a representation of the volume; and facilitating control, in response to at least one of a user input and the determined volume of the portion of fluid, of an operating parameter corresponding to the fluid reservoir to facilitate changing or maintaining the volume of the portion of fluid.

In an Example 16, the method of Example 15, further comprising providing, via a control panel having a display device and based on the image data, a graphical user interface (GUI), the GUI comprising a representation of the fluid flow reservoir, the representation of the fluid reservoir comprising a representation of the portion of fluid, the representation including a representation of the volume.

In an Example 17, the method of Example 16, wherein the representation of the fluid reservoir is an interactive representation, the method further comprising: receiving a user input associated with the interactive representation of the portion of fluid; and in response to receiving the user input, facilitating adjusting an operating parameter corresponding to the fluid reservoir to facilitate changing or maintaining the volume of the portion of fluid.

In an Example 18, the method of any of Examples 15-17, wherein the facilitating control of the operating parameter corresponding to the fluid reservoir comprises causing a heart lung machine (HLM) control unit to adjust an operating parameter corresponding to the fluid reservoir.

In an Example 19, the method of any of Examples 15-18, wherein the controller includes a heart lung machine (HLM) control unit, and wherein the HLM control unit is configured to adjust an operating parameter corresponding to the fluid reservoir.

In an Example 20, the method of either of Examples 18 or 19, wherein the HLM control unit is configured to control at least one of a venous clamp, a vacuum regulator, and an arterial pump.

In an Example 21, a perfusion system comprises: a fluid reservoir configured to hold a portion of fluid, the portion of fluid having a volume, the fluid reservoir having a total capacity that is greater than the volume; an imaging device, the imaging device configured to obtain image data corresponding to the fluid reservoir; and a controller configured to: receive the image data from the imaging device; determine the volume based on the image data; provide, via a control panel having a display device and based on the image data, a graphical user interface (GUI), the GUI comprising a representation of the fluid reservoir, the representation of the fluid reservoir comprising a representation of the portion of fluid, the representation including a representation of the volume; and cause, in response to at least one of a user input and the determined volume of the portion of fluid, a heart lung machine (HLM) control unit to control an operating parameter corresponding to the fluid reservoir to facilitate changing or maintaining the volume of the portion of fluid.

While multiple embodiments are disclosed, still other embodiments of the presently disclosed subject matter will become apparent to those skilled in the art from the following detailed description, which shows and describes illustrative embodiments of the disclosed subject matter. Accordingly, the drawings and detailed description are to be regarded as illustrative in nature and not restrictive.

Figure 1A:
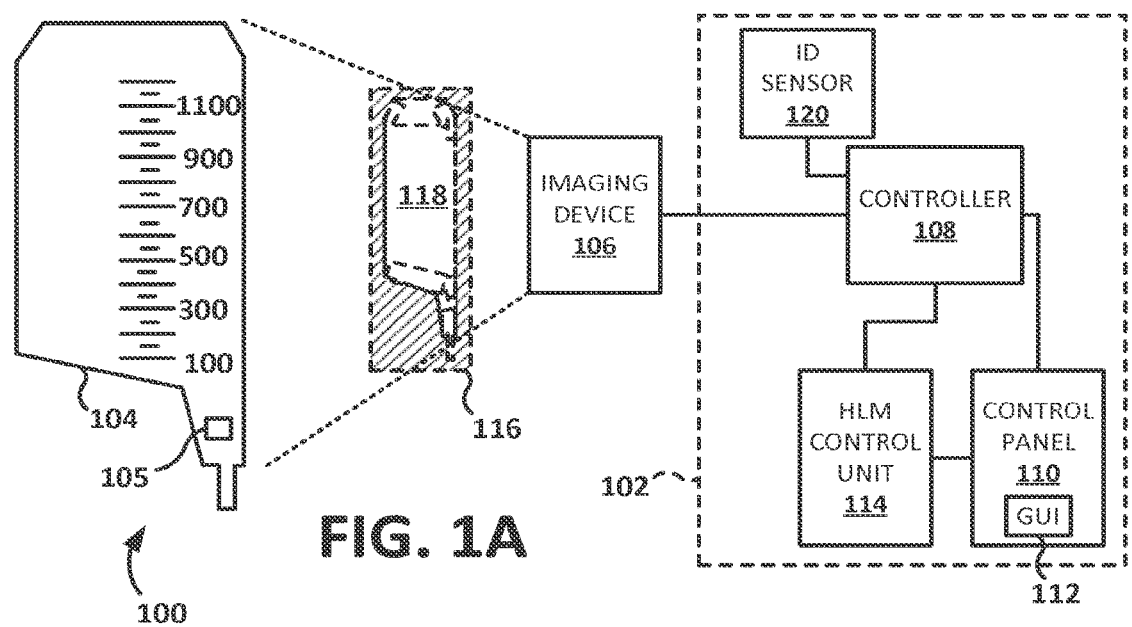
FIG. 1A is a schematic block diagram of an illustrative perfusion system, in accordance with embodiments of the disclosed subject matter.

While the disclosed subject matter is amenable to various modifications and alternative forms, specific embodiments have been shown by way of example in the drawings and are described in detail below. The intention, however, is not to limit the subject matter disclosed herein to the particular embodiments described. On the contrary, the disclosure is intended to cover all modifications, equivalents, and alternatives falling within the scope of the subject matter disclosed herein, and as defined by the appended claims.

As used herein in association with values (e.g., terms of magnitude, measurement, and/or other degrees of qualitative and/or quantitative observations that are used herein with respect to characteristics (e.g., dimensions, measurements, attributes, components, etc.) and/or ranges thereof, of tangible things (e.g., products, inventory, etc.) and/or intangible things (e.g., data, electronic representations of currency, accounts, information, portions of things (e.g., percentages, fractions), calculations, data models, dynamic system models, algorithms, parameters, etc.), "about" and "approximately" may be used, interchangeably, to refer to a value, configuration, orientation, and/or other characteristic that is equal to (or the same as) the stated value, configuration, orientation, and/or other characteristic or equal to (or the same as) a value, configuration, orientation, and/or other characteristic that is reasonably close to the stated value, configuration, orientation, and/or other characteristic, but that may differ by a reasonably small amount such as will be understood, and readily ascertained, by individuals having ordinary skill in the relevant arts to be attributable to measurement error; differences in measurement and/or manufacturing equipment calibration; human error in reading and/or setting measurements; adjustments made to optimize performance and/or structural parameters in view of other measurements (e.g., measurements associated with other things); particular implementation scenarios; imprecise adjustment and/or manipulation of things, settings, and/or measurements by a person, a computing device, and/or a machine; system tolerances; control loops; machine-learning; foreseeable variations (e.g., statistically insignificant variations, chaotic variations, system and/or model instabilities, etc.); preferences; and/or the like.

Although the term "block" may be used herein to connote different elements illustratively employed, the term should not be interpreted as implying any requirement of, or particular order among or between, various blocks disclosed herein. Similarly, although illustrative methods may be represented by one or more drawings (e.g., flow diagrams, communication flows, etc.), the drawings should not be interpreted as implying any requirement of, or particular order among or between, various steps disclosed herein. However, certain embodiments may require certain steps and/or certain orders between certain steps, as may be explicitly described herein and/or as may be understood from the nature of the steps themselves (e.g., the performance of some steps may depend on the outcome of a previous step). Additionally, a "set," "subset," or "group" of items (e.g., inputs, algorithms, data values, etc.) may include one or more items, and, similarly, a subset or subgroup of items may include one or more items. A "plurality" means more than one.

As used herein, the term "based on" is not meant to be restrictive, but rather indicates that a determination, identification, prediction, calculation, and/or the like, is performed by using, at least, the term following "based on" as an input. For example, predicting an outcome based on a particular piece of information may additionally, or alternatively, base the same determination on another piece of information.

DETAILED DESCRIPTION

Embodiments of the disclosure relate to an imaging device that can be used to monitor a blood level or blood volume in a blood reservoir. In embodiments, the imaging device can be utilized in an integrated perfusion system. In embodiments, the imaging device is focused on the fluid reservoir and able to provide and reproduce the image of the same on a graphical user interface (GUI) in real time. In embodiments, if the reservoir has volume graduations printed on its transparent body, the GUI image shows both blood level and volume, regardless of the reservoir shape and size. If not, embodiments of the image include only the blood level. In such a case, if the volume value is also desired, the level can be converted into volume, e.g., by considering the shape (e.g., geometry) of the fluid reservoir. This can be done in several ways.

For instance, a fluid reservoir database may include information associated with different types of reservoirs and, by detecting an identification (ID) indicator (or receiving a user input), (e.g., a QR code, barcode, RFID tag, etc.) using an ID sensor integrated in the imaging device and/or HLM, the type of reservoir may be identified and information about the reservoir ascertained based on the type of reservoir. In embodiments, the information about the reservoir may include a look-up table for converting levels into volumes. In embodiments, the use of an appropriate multiple optical sensor or digital camera as the imaging device may enable the system to reconstruct the image of the reservoir external shape and, based on that reconstruction, to convert the measured blood level into volume.

According to embodiments, the user (e.g., perfusionist) can interact with the GUI image such as, for example, by choosing and setting the level/volume at which blood is to be maintained in the reservoir. Also, minimum and/or maximum levels/volumes may be set by interacting with the GUI image and/or may be sent via a data connection or other interface to the device. In this manner, the desired amount of blood to be kept in the reservoir can be modified at any time. Embodiments of the system include autodiagnosis functionality that may be configured to facilitate avoiding an incorrect acquisition of information, which may lead to reservoir overflow, emptying, or false acquisitions. Embodiments of the system may also be used, for instance, in autotransfusion and other clinical applications, where the amount of blood or liquids contained into a reservoir are kept under automatic control by a processor regulating the blood or liquids entering and/or exiting the reservoir.

FIG. 1A is schematic block diagram depicting an illustrative perfusion system 100. According to embodiments, the perfusion system 100 includes a heart lung machine (HLM) 102, a fluid reservoir 104, an imaging device 106, and a controller 108. In some embodiments, the HLM 102 can be any type of HLM 102 and may include any number of different features. The fluid reservoir 104 may be configured to hold a portion of fluid, the portion of fluid having a volume. The fluid reservoir 104 may include a total capacity that is greater than the volume. In embodiments, the fluid reservoir 104 can be a venous blood reservoir, a vent blood reservoir, a cardiotomy or suction blood reservoir, and/or the like. In embodiments, the fluid reservoir 104 can be a blood reservoir that combines one or more of a venous blood reservoir, a vent reservoir, and/or a suction reservoir in a single structure. In embodiments, a sensor system includes the imaging device 106 (of which the curtain 116 may be an integral part), the controller 108, and the HLM control unit 114. In embodiments, the sensor system may also, or alternatively, include the control panel 110 and/or the GUI 112. In embodiments, the control panel 110 may be, be similar to, be included in, include, or otherwise correspond to the HLM control unit 114.

The imaging device 106 can be configured to periodically, continually, and/or continuously monitor a variable fluid level in the fluid reservoir 104. The imaging device 106 may be configured to obtain image data corresponding to the fluid reservoir 104. For example, in embodiments, the imaging device 106 may be, or include, a digital camera. In embodiments, the imaging device 106 may include any number of other optical sensors such as, for example, photoconductive sensors, photodiodes, phototransistors, photovoltaic sensors, charge coupled device (CCD) sensors, and/or the like. The imaging device may be coupled to a disposable component (e.g., the fluid reservoir 104), the HLM 102, the controller 108, and/or the like. In embodiments, the imaging device 106 may be a standalone device (and may include, e.g., a controller 108 and/or a control panel 110).

The controller 108 may be configured to receive the image data from the imaging device 106 and determine, based on the image data, the fluid level in the fluid reservoir 104, the fluid volume in the fluid reservoir 104, the volume of the fluid reservoir 104, and/or the like. In embodiments, the controller 108 may be configured to determine the fluid volume in the fluid reservoir 104 based on the image data as well as a known, or determined, shape of the fluid reservoir 104. According to embodiments, the volume of the portion of fluid in the fluid reservoir 104 may be precisely controlled with a combination of look up tables and control algorithms (e.g., control loop feedback mechanisms such as, for example, PIO algorithms), able to set and maintain the volume in the reservoir at a level requested by an operator or other system component.

In embodiments, the fluid reservoir 104 can include an ID indicator 105 (e.g., an RFID tag, a QRC code, barcode, etc.) that provides the controller 108 with information pertaining to the known geometry of the fluid reservoir 104. According to embodiments, information contained within an ID indicator 105 and/or disposed on the reservoir (e.g., a scale stamped on the reservoir) 104 may be used to facilitate fail safe acquisitions of images (e.g., via a verification procedure, authentication procedure, etc.), a capability of calculating blood volume based on a scale stamped onto a reservoir and/or geometrical information contained in the ID indicator 105, and/or the like. In embodiments, the volume of the fluid reservoir is calculated according to one or more of the techniques described in U.S. patent application Ser. No. 12/763,561, filed on Apr. 20, 2010, previously incorporated by reference herein. In some embodiments, the volume of the fluid reservoir 104 is calculated by integrating the level of blood in the reservoir against the known cross-sectional area of the fluid reservoir 104 at various heights throughout the fluid reservoir 104.

If the fluid reservoir 104 is a hard shell blood reservoir, the known geometry of the fluid reservoir 104 can include the cross-sectional area of the fluid reservoir 104, or a width and depth of the fluid reservoir 104 as well as details on how the cross-sectional area varies relative to height within the fluid reservoir 104. If the fluid reservoir 104 is a soft shell reservoir, the known geometry can be based at least in part upon a known lateral expansion rate of the soft shell reservoir relative to the blood level within the fluid reservoir 104.

In embodiments, the controller 108 may be configured to provide, via a control panel 110 having a display device and based on the image data, a graphical user interface (GUI) 112, the GUI 112 including a representation of the fluid reservoir, the representation of the fluid reservoir including a representation of the portion of fluid, the representation including a representation of the volume. According to embodiments, the controller 108 communicates with the control panel 110, which may be, include, or be included within any number of different combinations of input/output (I/O) devices. For example, in embodiments, a control panel 110 may include an input device that can be used by the perfusionist to enter information that is not otherwise entered into one or more of the HLM control units 114. An output device of the control panel 110 may be used by the HLM 102 to display pertinent information to the perfusionist. In embodiments, the I/O device may include a key pad, a keyboard, a touch screen, a monitor, communication via a data bus, and/or the like.

According to embodiments, the representations of the fluid reservoir and/or the portion of the fluid may include any number of different types of representations. For example, the representations may be indications (e.g., numerical values, small symbols, etc.), graphics (e.g., pictures, digitally created images, etc.), and/or the like. For example, in embodiments, the representation of the fluid reservoir is configured to resemble a fluid reservoir (e.g., the representation is a digitally-created depiction of the fluid reservoir, a photograph of the fluid reservoir, etc.), and, similarly, the representation of the volume may be configured to resemble the fluid within the fluid reservoir. That is, for example, the representation of the volume may include a fluid level depicted on the representation of the fluid reservoir.

According to embodiments, the representation of the fluid reservoir may include an interactive representation. That is, for example, the controller is configured to receive a user input associated with the interactive representation of the portion of fluid and, in response to receiving the user input, facilitate adjusting an operating parameter corresponding to the fluid reservoir to facilitate changing or maintaining the volume of the portion of fluid. In embodiments, for example, the user input is, or includes, manipulation, by a user of a feature of the interactive representation of the fluid reservoir. For example, the representation of the fluid reservoir may include an interactive representation of a fluid level that can be moved by the user via a user input device, where movement of the representation of the fluid level causes the fluid level set point to be changed. According to embodiments, the GUI may further include interactive representations configured to facilitate user selection of at least one of an alarm level, an alarm volume, a fluid volume set point, and/or the like. The interactive representations may include virtual sliders, knobs, dials, graphics, and/or the like.

In some embodiments, the controller 108 may be configured to facilitate controlling the HLM 102. For example, the controller 108 may be configured to facilitate control, in response to at least one of a user input and the determined volume of the portion of fluid, of an operating parameter corresponding to the fluid reservoir to facilitate changing or maintaining the volume of the portion of fluid. That is, for example, in embodiments the controller 108 may be, be similar to, include, or be included in an HLM control unit 114. In embodiments, the controller 108 is configured to facilitate control of the operating parameter corresponding to the fluid reservoir by adjusting the operating parameter corresponding to the fluid reservoir and/or by causing a heart lung machine (HLM) control unit 114 to adjust the operating parameter corresponding to the fluid, where the HLM control unit 114 is configured to facilitate control of an operating parameter of the HLM 102. According to embodiments, the HLM control unit 114 may be configured to control an operating parameter based on the at least one of the fluid level signal and the fluid volume signal. In embodiments, the HLM control unit 114 may be configured to control the operating parameter by controlling at least one of a venous clamp, a vacuum regulator, and an arterial pump.

As indicated above, while the controller 108 is shown as a distinct element and can be a standalone controller, in embodiments, the controller 108 may include an HLM control unit 114, be included in an HLM control unit 114, be included in the imaging device 106, and/or the like. In embodiments, the HLM control unit 114 may represent one or more control units associated with an HLM including, for example, control units corresponding to individual operational components (e.g., control units corresponding to pump modules), a main control unit, and/or the like. For example, in embodiments, the HLM 102 may include a number of pump modules, each of which includes a corresponding HLM control unit 114. In embodiments, each HLM control unit 114 may be configured to operate and monitor the operation of the corresponding pump module. In some embodiments, each HLM control unit 114 includes one or more input devices (not illustrated), such as switches, knobs, buttons, and touch screens, so the perfusionist can adjust the operation of the corresponding pump module.

Figure 1B:
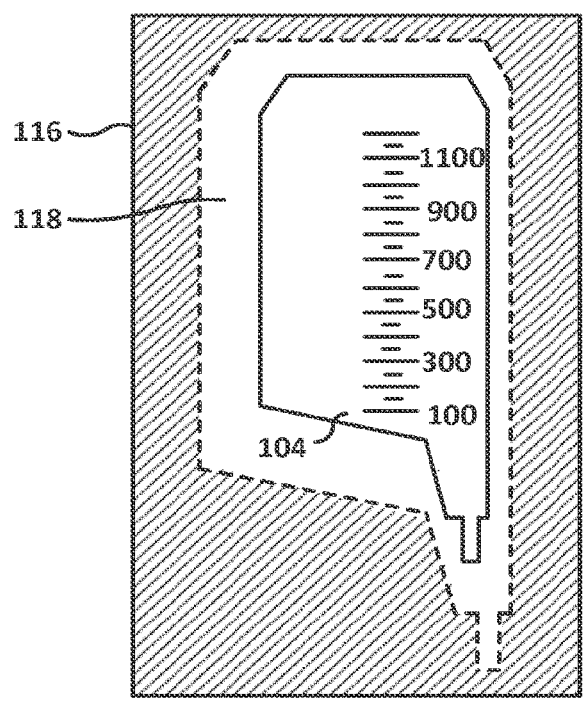
FIG. 1B is a schematic diagram of an illustrative curtain, in accordance with embodiments of the disclosed subject matter.

In embodiments, the imaging device 106 may create a virtual curtain around the shape of the reservoir to facilitate obtaining a reference point to prevent false acquisitions in case the imaging device 106 is accidentally moved away from the reservoir 104 or a foreign object is introduced into the line of sight of the camera. As shown in FIGS. 1A and 1B, the perfusion system 100 may include a virtual curtain 116. FIG. 1A is a schematic diagram of the illustrative virtual curtain 116 depicted in FIG. 1A in accordance with embodiments of the subject matter disclosed herein. The virtual curtain 116 is may include an opening 118 disposed therethrough, the opening 118 having a shape that corresponds to a shape of the fluid reservoir 104 such that the curtain 116 is configured to facilitate positioning of the imaging device 106 in relation to the fluid reservoir 104. Accordingly, the virtual curtain 116 may be considered to be an integral part of the safety functions and control system of the imaging device 106. In embodiments, an alarm may be generated in response to detecting, based on a captured image of the curtain and fluid reservoir, that the imaging device 106 is not appropriately positioned. According to embodiments, the curtain 116 also may serve as a barrier to prevent false acquisitions due to foreign objects entering into the optical pathway between the fluid reservoir and the imaging device 106.

According to embodiments, the perfusion system 100 may be self-monitoring and/or diagnosing. That is, for example, the controller 108 may be configured to facilitate control of an operating parameter corresponding to the fluid reservoir to facilitate continually changing the volume of the portion of fluid about a fluid volume set point. In embodiments, the controller 108 sends a signal to a functional component (e.g., the pump, electrical clamp, vacuum controller, etc.) in order to vary the fluid in the reservoir 104. If the imaging device and/or optical sensor does not detect a variation of the fluid level within a predetermined amount of time, an alarm signal may be generated to indicate a fault in the regulation system.

Figure 2:
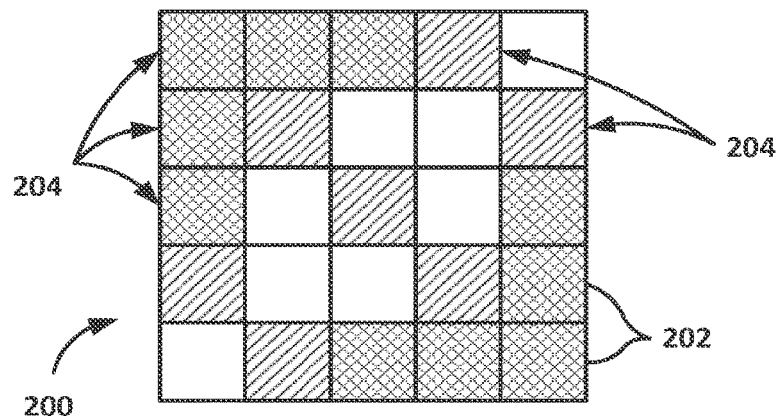
FIG. 2 depicts an illustrative pixel test pattern, in accordance with embodiments of the disclosed subject matter.

In embodiments, the controller 108 may be configured to write a pixel test pattern to an imaging device memory; and to determine, whether, during a next data acquisition cycle, the pixel test pattern is replaced with an acquired image. FIG. 2 depicts an illustrative pixel test pattern 200, in accordance with embodiments of the subject matter disclosed herein. As shown in FIG. 2, for example, embodiments of the pixel test pattern 200 include a pattern of pixels 202 having one or more pixel groups 204 having values of at least one of color and intensity that are not expected to occur naturally in the imaging environment. In embodiments, the pixel test pattern may be utilized as part of a security function to determine whether the virtual system is updating the acquired images correctly.

Figure 3:
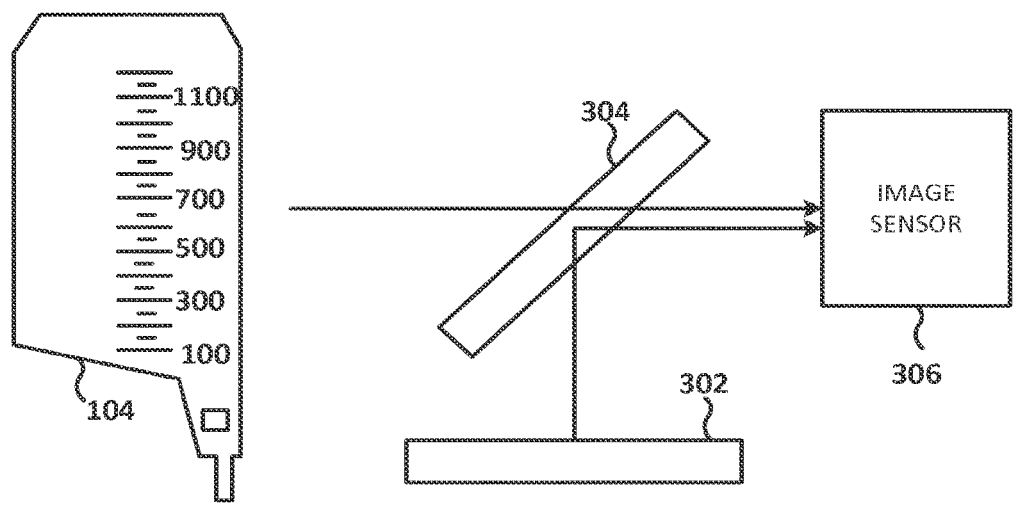
FIG. 3 is a schematic diagram depicting an illustrative process for detecting frozen images, in accordance with embodiments of the disclosed subject matter.

In embodiments, the controller 108 may be configured to detect frozen images by using an image test pattern. FIG. 3 is a schematic diagram depicting an illustrative process for detecting frozen images in accordance with embodiments of the subject matter disclosed herein. In embodiments, as shown in FIG. 3, the controller 108 may be configured to generate an image test pattern 302; and to cause, using an optical mixer 304, the image test pattern to be projected on an image sensor 306 of the imaging device together with the image data. In embodiments, the image data includes a pattern associated with the fluid reservoir. The controller 108 may be further configured to compare the image test pattern to the pattern associated with the fluid reservoir, where, if the image test pattern is at least approximately identical to the pattern associated with the fluid reservoir, the controller is configured to determine that the image data is not associated with a frozen image and may, for example, be configured to accept the image data. In embodiments, for example, the image test pattern may include a digital clock that is compared to a representation of a digital clock generated by the controller 108.

With continued reference to FIG. 1A, the HLM 102 may further include an ID sensor 120 configured to detect and/or otherwise obtain information from, or corresponding to, the ID indicator 105. In embodiments, for example, the ID sensor 120 may include a barcode reader, a QR code reader, or optical information reader, and the ID indicator 105 may include a barcode, QR code, or other optical information. The ID indicator 105 may be part of the fluid reservoir 104 and programmed with or otherwise configured to include a variety of information pertaining to the fluid reservoir 104. In some embodiments, the ID indicator 105 can be adhesively secured to the fluid reservoir 104. In some embodiments, the ID indicator 105 can be molded into the fluid reservoir 104. In embodiments, the ID indicator 105 can be printed onto the fluid reservoir 104.

In embodiments, the ID indicator 105 may include data or identifying information for the fluid reservoir 104, such as the name of the particular fluid reservoir 104, a reference code, a serial number, a lot number, an expiration date, and/or the like. In embodiments, this information may be communicated to the controller 108 and used to confirm that the proper fluid reservoir 104 is being used for a particular setting or patient. For example, the controller 108 may recognize that a pediatric blood reservoir of a certain model is being used in combination with an adult-sized blood reservoir or the controller 108 may recognize that an expected component is missing. The controller 108 may be configured to recognize potential mismatches in equipment as a result of the information provided by the ID indicator 105 attached to each of the one or more fluid reservoirs 104.

In some embodiments, the ID indicator 105 may include descriptive or design information for the fluid reservoir 104, such as materials, a list of components, priming volume of a component or tubing circuit, tubing size, tubing length, minimum and maximum working pressures, minimum and maximum working volume, and blood reservoir sizing information, such as blood reservoir dimensions. In some embodiments, this information can be communicated to the controller 108 and used by the controller 108 to at least partially configure and/or operate the HLM 102. For example, the controller 108 may be configured to use the sizing information provided from each of the fluid reservoirs 104 to determine a working blood volume for the HLM 102.

In embodiments, the controller 108 may be configured to provide level control within the fluid reservoir 104. For example, the reservoir 104 may be provided with one or more level sensors (e.g., the imaging device 106) configured to sense a level of blood and/or other fluid within the reservoir 104. The sensed level can be used to activate alarms at the user interface indicative of, for example, full reservoir, empty reservoir, low level, and/or the like. The sensed level can also be used in the closed loop feedback control of other parts of a perfusion system which affect (and/or are affected by) the level of blood in the reservoir 104. For example, in embodiments portions of an HLM 102 may be controlled based on sensed parameters such as, for example, pressure, level, temperature, and/or the like.

According to embodiments, the controller 108, the control panel 110, the HLM control unit 114, and/or the imaging device 106, may include a processing unit configured to communicate with memory to execute computer-executable instructions stored in the memory. In embodiments, for example, the controller 108 may be, include, or be included in one or more Field Programmable Gate Arrays (FPGAs), one or more Programmable Logic Devices (PLDs), one or more Complex PLDs (CPLDs), one or more custom Application Specific Integrated Circuits (ASICs), one or more dedicated processors (e.g., microprocessors), one or more central processing units (CPUs), software, hardware, firmware, or any combination of these and/or other components. Although each of the controller 108, the control panel 110, the HLM control unit 114, and the imaging device 106 is referred to herein in the singular, the controller 108, the control panel 110, the HLM control unit 114, and/or the imaging device 106 may be implemented in multiple instances, distributed across multiple computing devices, instantiated within multiple virtual machines, and/or the like.

As indicated above, the control panel 100 may include one or more I/O devices, which may include any number of different types of I/O devices such as, for example, light indicators, speakers, buttons, and/or the like. The I/O device(s) may be configured to present information to a user and/or receive input from a user. According to embodiments, the I/O device may be configured to indicate a device status (e.g., on/off, active, error, etc.), receive a command from a user, and/or the like. In embodiments, the I/O device may include a touch-screen interface, an LED, and/or the like.

According to various embodiments of the disclosed subject matter, any number of the components depicted in FIG. 1A (e.g., the controller 108, the control panel 110, the HLM control unit 114, the imaging device 106, etc.), may be implemented on one or more computing devices. A computing device may include any type of computing device suitable for implementing aspects of embodiments of the disclosed subject matter. Examples of computing devices include specialized computing devices or general-purpose computing devices such "workstations," "servers," "laptops," "desktops," "tablet computers," "hand-held devices," "portable sampling devices," and the like, all of which are contemplated within the scope of FIG. 1A, with reference to various components of the system 100.

In embodiments, a computing device includes a bus that, directly and/or indirectly, couples the following devices: a processing unit, a memory, an input/output (I/O) port, an I/O component, and a power supply. Any number of additional components, different components, and/or combinations of components may also be included in the computing device. The I/O component may include a presentation component configured to present information to a user such as, for example, a display device, a speaker, a printing device, and/or the like, and/or an input component such as, for example, a microphone, a joystick, a satellite dish, a scanner, a printer, a wireless device, a keyboard, a pen, a voice input device, a touch input device, a touch-screen device, an interactive display device, a mouse, and/or the like.

The bus represents what may be one or more busses (such as, for example, an address bus, data bus, or combination thereof). Similarly, in embodiments, the computing device may include a number of processing units, a number of memory components, a number of I/O ports, a number of I/O components, and/or a number of power supplies. Additionally any number of these components, or combinations thereof, may be distributed and/or duplicated across a number of computing devices.

In embodiments, the memory includes computer-readable media in the form of volatile and/or nonvolatile memory and may be removable, nonremovable, or a combination thereof. Media examples include Random Access Memory (RAM); Read Only Memory (ROM); Electronically Erasable Programmable Read Only Memory (EEPROM); flash memory; optical or holographic media; magnetic cassettes, magnetic tape, magnetic disk storage or other magnetic storage devices; data transmissions; and/or any other medium that can be used to store information and can be accessed by a computing device such as, for example, quantum state memory, and/or the like. In embodiments, the memory stores computer-executable instructions for causing the processor to implement aspects of embodiments of system components discussed herein and/or to perform aspects of embodiments of methods and procedures discussed herein.

The computer-executable instructions may include, for example, computer code, machine-useable instructions, and the like such as, for example, program components capable of being executed by one or more processors associated with the computing device. Program components may be programmed using any number of different programming environments, including various languages, development kits, frameworks, and/or the like. Some or all of the functionality contemplated herein may also, or alternatively, be implemented in hardware and/or firmware The illustrative perfusion system 100 shown in FIGS. 1A and 1B is not intended to suggest any limitation as to the scope of use or functionality of embodiments of the present disclosure. The illustrative system 100 also should not be interpreted as having any dependency or requirement related to any single component or combination of components illustrated therein. Additionally, various components depicted in FIG. 1A may be, in embodiments, integrated with various ones of the other components depicted therein (and/or components not illustrated), all of which are considered to be within the ambit of the present disclosure.

Figure 4:
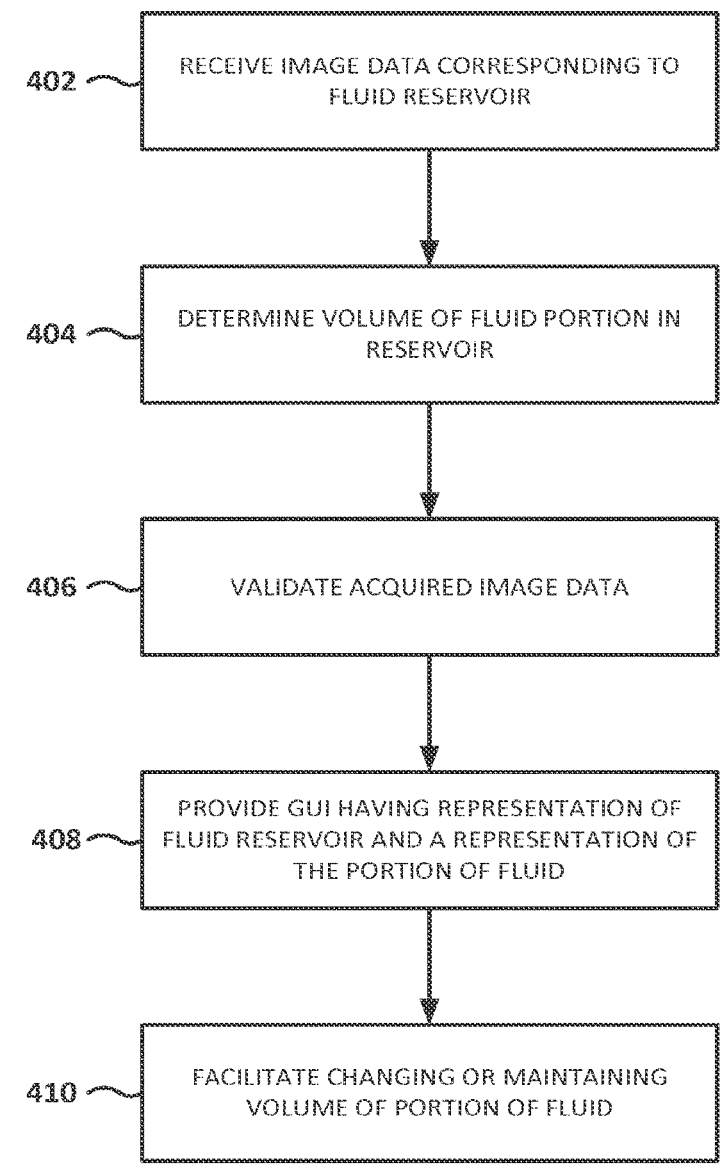
FIG. 4 is a flow diagram depicting an illustrative method of performing perfusion, in accordance with embodiments of the disclosed subject matter.

FIG. 4 is a flow diagram depicting an illustrative method 400 of performing perfusion, using a perfusion system having a fluid reservoir configured to hold a portion of fluid, the portion of fluid having a volume. According to embodiments, aspects of the method 400 may be performed by a controller such as, for example, the controller 108 depicted in FIG. 1A. As shown in FIG. 4, embodiments of the method 400 include receiving, by a controller and from an imaging device, image data corresponding to the fluid reservoir (block 402). For example, in embodiments, the imaging device may include a digital camera, optical sensor, and/or the like.

Embodiments of the method 400 further include determining the volume based on the image data (block 404); validating the acquired image data (block 406); and providing, via a control panel having a display device and based on the image data, a graphical user interface (GUI), the GUI comprising a representation of the fluid reservoir, the representation of the fluid reservoir comprising a representation of the portion of fluid, the representation including a representation of the volume (block 408). In embodiments, the representation of the fluid reservoir is an interactive representation, and the method 400 includes receiving a user input associated with the interactive representation of the portion of fluid; and in response to receiving the user input, facilitating adjusting an operating parameter corresponding to the fluid reservoir to facilitate changing or maintaining the volume of the portion of fluid.

As shown in FIG. 4, embodiments of the method 400 include facilitating control, in response to at least one of a user input and the determined volume of the portion of fluid, of an operating parameter corresponding to the fluid reservoir to facilitate changing or maintaining the volume of the portion of fluid (block 410). In embodiments, facilitating control of the operating parameter corresponding to the fluid reservoir includes causing a heart lung machine (HLM) control unit to adjust an operating parameter corresponding to the fluid reservoir. In other embodiments, the control unit includes a heart lung machine (HLM) control unit, and the HLM control unit is configured to adjust an operating parameter corresponding to the fluid reservoir.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

We claim:

1. A cardiopulmonary bypass perfusion system, comprising:
a fluid reservoir configured to hold a fluid, the fluid reservoir including a radio-frequency identification (RFID) tag;
an imaging device including an identification sensor configured to detect the RFID tag corresponding to the fluid reservoir; and
a controller in communication with the imaging device;
wherein the imaging device is configured to provide information pertaining to the fluid reservoir from the RFID tag to the controller.

2. The cardiopulmonary bypass perfusion system of claim 1, wherein the controller is configured to determine a fluid volume of the fluid reservoir based on the information.

3. The cardiopulmonary bypass perfusion system of claim 2, wherein the controller is further configured to provide, via a control panel having a display device and based on the image data, a graphical user interface (GUI), the GUI comprising a representation of the fluid volume.

4. The cardiopulmonary bypass perfusion system of claim 3, wherein the GUI further comprises interactive representations configured to facilitate user selection of at least one of an alarm level, an alarm volume, and a fluid volume set point.

5. The cardiopulmonary bypass perfusion system of claim 1, wherein the controller is configured to receive a user input associated with the fluid to adjust an operating parameter corresponding to the fluid reservoir to facilitate changing or maintaining a volume of the fluid within the fluid reservoir.

6. The cardiopulmonary bypass perfusion system of claim 1, wherein the controller is configured to determine a known geometry of the fluid reservoir based on the information.

7. The cardiopulmonary bypass perfusion system of claim 6, wherein the known geometry includes a shape of the fluid reservoir.

8. The cardiopulmonary bypass perfusion system of claim 7, wherein the controller is configured to determine a volume of the fluid within the fluid reservoir based on image data associated with an image region having a shape that corresponds to the shape of the fluid reservoir.

9. The cardiopulmonary bypass perfusion system of claim 6, wherein the known geometry includes a capacity of the fluid reservoir.

10. The cardiopulmonary bypass perfusion system of claim 1, wherein the controller includes a fluid reservoir database including information associated with different types of fluid reservoirs and detecting the RFID tag with the identification sensor ascertains the type of the fluid reservoir.

11. The cardiopulmonary bypass perfusion system of claim 10, wherein the information associated with the fluid reservoir includes a look-up table for converting levels of the fluid into volumes of the fluid.

12. The cardiopulmonary bypass perfusion system of claim 1, wherein the RFID tag includes data associated with the fluid reservoir, the data comprising at least one of a name, a reference code, a serial number, a lot number, and an expiration date.

13. The cardiopulmonary bypass perfusion system of claim 12, wherein the controller is configured to use the data to confirm the fluid reservoir is correct to use for a selected setting.

14. The cardiopulmonary bypass perfusion system of claim 12, wherein the controller is configured to detect potential mismatches in equipment within the cardiopulmonary bypass perfusion system as a result of the data included in the RFID tag.

15. The cardiopulmonary bypass perfusion system of claim 1, wherein the RFID tag includes design information associated with the fluid reservoir, the design information comprising at least one of materials, a list of components, priming volume of a component or tubing circuit, tubing size, tubing length, minimum and maximum working pressures, minimum and maximum working volumes, and fluid reservoir dimensions.

16. The cardiopulmonary bypass perfusion system of claim 15, wherein controller is configured to use the design information to at least partially configure or operate a heart lung machine associated with the cardiopulmonary bypass perfusion system.

17. The cardiopulmonary bypass perfusion system of claim 16, wherein the controller includes a control unit for the heart lung machine, the control unit being configured to control at least one of a venous clamp, a vacuum regulator, and an arterial pump of the heart lung machine.

18. A cardiopulmonary bypass perfusion system, comprising:
   a fluid reservoir configured to hold a fluid, the fluid reservoir including a radio-frequency identification (RFID) tag;
   an imaging device including an identification sensor configured to detect the RFID tag corresponding to the fluid reservoir; and
   a controller in communication with the imaging device;
   wherein the imaging device is configured to provide information pertaining to the fluid reservoir from the RFID tag to the controller;
   wherein the imaging device comprises a virtual curtain having an opening disposed therethrough, the opening having a shape that corresponds to the shape of the fluid reservoir, wherein the virtual curtain is configured to facilitate positioning of the imaging device in relation to the fluid reservoir.

19. A cardiopulmonary bypass perfusion system, comprising:
   a fluid reservoir configured to hold a fluid, the fluid reservoir including a radio-frequency identification (RFID) tag;
   an imaging device including an identification sensor configured to detect the RFID tag corresponding to the fluid reservoir; and
   a controller in communication with the imaging device;
   wherein the imaging device is configured to provide information pertaining to the fluid reservoir from the RFID tag to the controller;
   wherein controller is configured to use the information to at least partially configure or operate a heart lung machine associated with the cardiopulmonary bypass perfusion system.

20. The cardiopulmonary bypass perfusion system of claim 19, wherein the controller includes a control unit for the heart lung machine, the control unit being configured to control at least one of a venous clamp, a vacuum regulator, and an arterial pump of the heart lung machine.

* * * * *